US011419581B2

(12) United States Patent
Vignon et al.

(10) Patent No.: US 11,419,581 B2
(45) Date of Patent: Aug. 23, 2022

(54) TRIPLE MODE ULTRASOUND IMAGING FOR ANATOMICAL, FUNCTIONAL, AND HEMODYNAMICAL IMAGING

(71) Applicant: KONINKLIJKE PHILIPS N.V., Eindhoven (NL)

(72) Inventors: Francois Guy Gerard Marie Vignon, Andover, MA (US); Sheng-Wen Huang, Ossining, NY (US); Oudom Somphone, Paris (FR); Scott William Dianis, Andover, MA (US); Lea Melki, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 329 days.

(21) Appl. No.: 16/347,599

(22) PCT Filed: Nov. 14, 2017

(86) PCT No.: PCT/EP2017/079220
§ 371 (c)(1),
(2) Date: May 6, 2019

(87) PCT Pub. No.: WO2018/087400
PCT Pub. Date: May 17, 2018

(65) Prior Publication Data
US 2019/0254630 A1 Aug. 22, 2019

(30) Foreign Application Priority Data
Nov. 14, 2016 (EP) .................................... 16306484

(51) Int. Cl.
*A61B 8/00* (2006.01)
*A61B 8/08* (2006.01)
(Continued)

(52) U.S. Cl.
CPC .............. *A61B 8/463* (2013.01); *A61B 8/485* (2013.01); *A61B 8/486* (2013.01); *A61B 8/488* (2013.01);
(Continued)

(58) Field of Classification Search
CPC ......... A61B 8/463; A61B 8/485; A61B 8/486; A61B 8/488; A61B 8/5207;
(Continued)

(56) References Cited

U.S. PATENT DOCUMENTS 5,090,411 A * 2/1992 Higuchi .................. A61B 8/06
600/440
6,139,501 A * 10/2000 Roundhill ........... G01S 7/52074
600/443
(Continued)

FOREIGN PATENT DOCUMENTS

| JP | 2001299765 A | 10/2001 |
|----|--------------|---------|
| JP | 2004000620 A | 1/2004 |

(Continued)

OTHER PUBLICATIONS

Provost et al, "Electromechanical Wave Imaging for Arrhythmias", Phys. Med. Biol. 56 L1-L11 (Jan. 12, 2011).
(Continued)

*Primary Examiner* — Amanda Lauritzen Moher
*Assistant Examiner* — Nyrobi Celestine

(57) ABSTRACT

An ultrasonic imaging system acquires frames of echo data at a high acquisition frame rate using a single mode of acquisition. The echo data is used by three image processors to produce an anatomical image, a mechanical function image, and a hemodynamic image from the same echo data. A display displays an anatomical image, a mechanical function image, and a hemodynamic image simultaneously.

14 Claims, 8 Drawing Sheets

(51) Int. Cl.
*G01S 7/52* (2006.01)
*G01S 15/89* (2006.01)
*G16H 30/40* (2018.01)
*A61B 8/06* (2006.01)

(52) U.S. Cl.
CPC ........ *A61B 8/5207* (2013.01); *G01S 7/52042* (2013.01); *G01S 7/52071* (2013.01); *G01S 7/52095* (2013.01); *G01S 15/89* (2013.01); *G01S 15/8915* (2013.01); *G01S 15/8979* (2013.01); *G01S 15/8981* (2013.01); *A61B 8/06* (2013.01); *A61B 8/08* (2013.01); *G01S 7/52074* (2013.01); *G01S 15/8988* (2013.01); *G16H 30/40* (2018.01)

(58) Field of Classification Search
CPC .... G01S 7/52042; G01S 7/52071; G01S 5/89; G01S 5/8915; G01S 5/8981; G01S 7/52074; G01S 5/8988; G01S 7/52095; G16H 30/40
See application file for complete search history.

(56) References Cited

U.S. PATENT DOCUMENTS

| | | | | |
|---|---|---|---|---|
| 6,390,980 | B1* | 5/2002 | Peterson | G01S 15/8995 600/443 |
| 6,589,177 | B1 | 7/2003 | Detmer et al. | |
| 9,398,898 | B2* | 7/2016 | Wilkening | G01S 7/52088 |
| 9,629,615 | B1* | 4/2017 | Tavakoli | G06T 7/269 |
| 9,895,138 | B2* | 2/2018 | Sasaki | G01S 7/52073 |
| 10,517,564 | B2* | 12/2019 | Konofagou | A61B 8/5223 |
| 2007/0055158 | A1* | 3/2007 | Jackson | A61B 8/08 600/443 |
| 2007/0239001 | A1 | 10/2007 | Mehi et al. | |
| 2007/0276237 | A1* | 11/2007 | Li | G01S 15/8925 600/437 |
| 2008/0234580 | A1* | 9/2008 | Bruce | A61B 8/463 600/441 |
| 2009/0069693 | A1* | 3/2009 | Burcher | G01S 15/8995 600/459 |
| 2010/0152578 | A1* | 6/2010 | Hall | A61B 8/467 600/437 |
| 2010/0240994 | A1 | 9/2010 | Zheng | |
| 2011/0245678 | A1* | 10/2011 | Tamura | A61B 8/485 600/453 |
| 2012/0287156 | A1* | 11/2012 | Tsujita | G01S 7/52071 345/629 |
| 2013/0184580 | A1* | 7/2013 | Lause | G01S 7/52066 600/440 |
| 2013/0345564 | A1 | 12/2013 | Nakaya et al. | |
| 2014/0128738 | A1* | 5/2014 | White | A61B 8/543 600/447 |
| 2015/0087980 | A1* | 3/2015 | Yao | G01S 7/52038 600/440 |
| 2015/0133782 | A1* | 5/2015 | Yoshikawa | A61B 8/5223 600/438 |
| 2016/0030005 | A1* | 2/2016 | Kulakowski, Jr. | A61B 8/4455 600/438 |
| 2016/0089114 | A1* | 3/2016 | Kim | A61B 8/488 600/441 |
| 2016/0228091 | A1* | 8/2016 | Chiang | G16H 40/67 |
| 2017/0128046 | A1* | 5/2017 | Kim | A61B 8/462 |
| 2017/0290570 | A1 | 10/2017 | Yamamoto | |
| 2018/0028154 | A1* | 2/2018 | Zhai | A61B 8/5207 |
| 2018/0146952 | A1 | 5/2018 | Du et al. | |

FOREIGN PATENT DOCUMENTS

| | | | | |
|---|---|---|---|---|
| JP | 2005348758 | A | 12/2005 | |
| JP | 2012110527 | A | 6/2012 | |
| JP | 2014042823 | A | 3/2014 | |
| JP | 2016042960 | A | 4/2016 | |
| WO | WO-2007107926 | A1* | 9/2007 | ............. A61B 8/488 |
| WO | WO-2011027253 | A1* | 3/2011 | ......... G01S 7/52084 |
| WO | 2014021402 | A1 | 2/2014 | |

OTHER PUBLICATIONS

Couade et al, "Ultrafast imaging of the heart using Circular Wave Synthetic Imaging with Phased Arrays", IUS symposium, pp. 515-518 (2009).

Kanai, "Propagation of vibration caused by electrical excitation in the normal human heart.", Ultrasound in Med. & Biol. vol. 35(6), p. 935-946 (2009).

Osmanski et al, "Transthoracic ultrafast Doppler of human left ventricular hemodynamic function", IEEE TUFFC 61(8) Aug. 2014.

Nillesen et al, "Segmentation of 3D cardiac ultrasound images using correlation of radio frequency data", IEEE ISBI Symposium , p. 522-525 (2009).

Bercoff et al, "Ultrafast compound Doppler imaging: providing full blood flow characterization", IEEE TUFFC 58(1), Jan. 2011.

Vignon and Burcher, "Capon beamforming in medical imaging with focused beams", IEEE TUFFC 55(3), 619-28, Mar. 2008.

Tanter and Fink, "Ultrafast Imaging in Medical Ultrasound", IEEE TUFFC vol. 61(1), p. 102-119; Jan. 2014.

International Search Report and Written Opinion dated Feb. 9, 2018.

* cited by examiner

TRIPLE MODE ULTRASOUND IMAGING FOR ANATOMICAL, FUNCTIONAL, AND HEMODYNAMICAL IMAGING

CROSS-REFERENCE TO PRIOR APPLICATIONS

This application is the U.S. National Phase application under 35 U.S.C. § 371 of International Application No. PCT/EP2017/079220, filed on Nov. 14, 2017, which claims the benefit of EP Patent Application No. EP 16306484.3, filed on Nov. 14, 2016. These applications are hereby incorporated by reference herein.

FIELD OF THE INVENTION

This invention relates to medical diagnostic ultrasound and, in particular, to triple mode ultrasonic imaging of anatomical structure, mechanical function and hemodynamics.

BACKGROUND OF THE INVENTION

Ultrasound imaging enables assessment of structural and functional characteristics of tissue and organs of the body. B mode imaging provides anatomical information and volume quantification. Tissue motion and deformation (tissue velocity, displacement, strain, strain rate) provides information about myocardial function as it relates to ischemia and conduction disorders. Blood flow imaging modes (spectral Doppler, color Doppler, power Doppler, B-flow and vector Flow) provide information on hemodynamics.

Currently, B mode measurements are done on images acquired with high beam density for high image quality. Tissue motion and deformation imaging and blood flow estimation are performed in special Doppler modes interleaved with B mode acquisition in order to have fast transmit pulse repetition rates which facilitates estimation of motion. These different modes use specific transmit pulse sequences that are unique for each mode. The interleave of these sequences can be line-by-line or frame-by-frame. The need to interleave transmission for the different modes degrades the ability to perform B mode, blood flow, and tissue motion measurements simultaneously. If a physician want to assess cardiac anatomy, cardiac strain, and blood flow dynamics, he or she has to use three separate modes sequentially, i.e., operationally interleaved. The workflow to perform these modes is complex. In addition, the resulting information may not be spatially and temporally registered, as probe and patient motion may occur during the different mode acquisitions, causing the information to relate to different heart phases and even different cardiac cycles. Accordingly it is desirable to image in three different ultrasound modes simultaneously.

U.S. Pat. No. 6,589,177 is directed to an ultrasound imaging system and method that simultaneously forms a B-mode volume and B-flow volume from the same set of transmit beams. When forming 3D volumes, the image data is usually reduced to a lower sampling density than the original image data (typically a maximum of 256 samples in any dimension, given current processing capabilities). Thus, limitations in image quality or flow quality due to tradeoffs for efficiency can be tolerated to some degree.

WO2000/075689 discloses multi-mode ultrasonic images that are formed by processing the ultrasonic echoes from a single transmit pulse in parallel to display both tissue and motion. In a preferred embodiment short transmit bursts are employed to produce echo ensembles for tissue motion imaging. At least one sequence of echoes of the ensemble is also B mode processed for display of tissue structure. Preferably both the B mode and motion processing are performed in parallel. A substantially constant pulse repetition frequency reduces artifact development when imaging in the two modes from the same transmit pulse.

WO2007/056104 discloses a system for acquiring an ultrasound signal comprises a signal processing unit adapted for acquiring a received ultrasound signal from an ultrasound transducer having a plurality of elements. The system is adapted to receive ultrasound signals having a frequency of at least 20 megahertz (MHz) with a transducer having a field of view of at least 5.0 millimeters (mm) at a frame rate of at least 20 frames per second (fps). The signal processing can further produce an ultrasound image from the acquired ultrasound signal. The transducer can be a linear array transducer, a phased array transducer, a two-dimensional (2-D) array transducer, or a curved array transducer.

WO2014/021042 discloses an ultrasound diagnostic device according to one embodiment is provided with an ultrasonic probe (1) and a control unit (18). The ultrasonic probe (1) transmits and receives ultrasonic waves. The control unit (18) causes the ultrasonic probe (1) to implement a first ultrasonic scan for acquiring information pertaining to the movement of a moving body within a first scanning range, and causes the ultrasonic probe (1) to implement a second ultrasonic scan for acquiring information pertaining to the form of the tissue in a second scanning region, in which the second scanning region is divided into a plurality of divided regions and each of the sub-regions is subjected to an ultrasonic scan in the periods between the first ultrasonic scans. The first ultrasonic scan implemented by the control unit (18) is based on a method in which the reception signals acquired for each of the plurality of scanning lines that form the first scanning range are subjected to high-pass filtering in the frame direction, and information pertaining to the movement of the moving body is acquired.

SUMMARY OF THE INVENTION

In accordance with the principles of the present invention, triple mode ultrasound imaging is done using very high frame acquisition rates, typically 800 Hz or greater, which can be achieved by storing the acquired frames in a frame memory that is used for all three image modes of the triple mode ultrasound system. Insonification of the image field is done with diverging (e.g., weakly focused) transmit beams, and high order multiline acquisition is employed. Optionally, coherent compounding of successive transmit beams can be employed. The high acquisition frame rates enable received frames to be coherently combined to enhance signal to noise ratio with little degradation in resolution, and allow accurate velocity measurements. Frames may correspond to an image field of view that has a depth into the tissue and width depending on the dimensions of the transducer and/or the beam profile. Frames can be 2D or 3D. Using frames can enable motion estimation calculations on 2D or 3D kernels that can, e.g., decrease noise for motion estimate calculations. Preferably anatomical imaging, mechanical function, and blood flow measurement are done simultaneously using a common transmit pulse sequence. The high frame acquisition rate enables the use of arbitrarily (e.g., infinite) long echo ensemble lengths for velocity imaging and measurement and allow many displacement estimates to be combined into one. For example, ensemble lengths correspond to the number of frames used to produce one motion estimate. Different ensemble lengths may be desired for different imaging modes, e.g., longer ensemble lengths may be needed for Color Doppler imaging as compared to tissue motion imaging. Moreover, the coherence from frame to frame enables the use of frame averaging for enhanced anatomical imaging while surrounding blood flow de-correlates. The three simultaneous modes of imaging can be used to assess muscular function and hemodynamics at the same time and interactions between the two can be studied in detail.

DETAILED DESCRIPTION OF EMBODIMENTS

Figure 1:
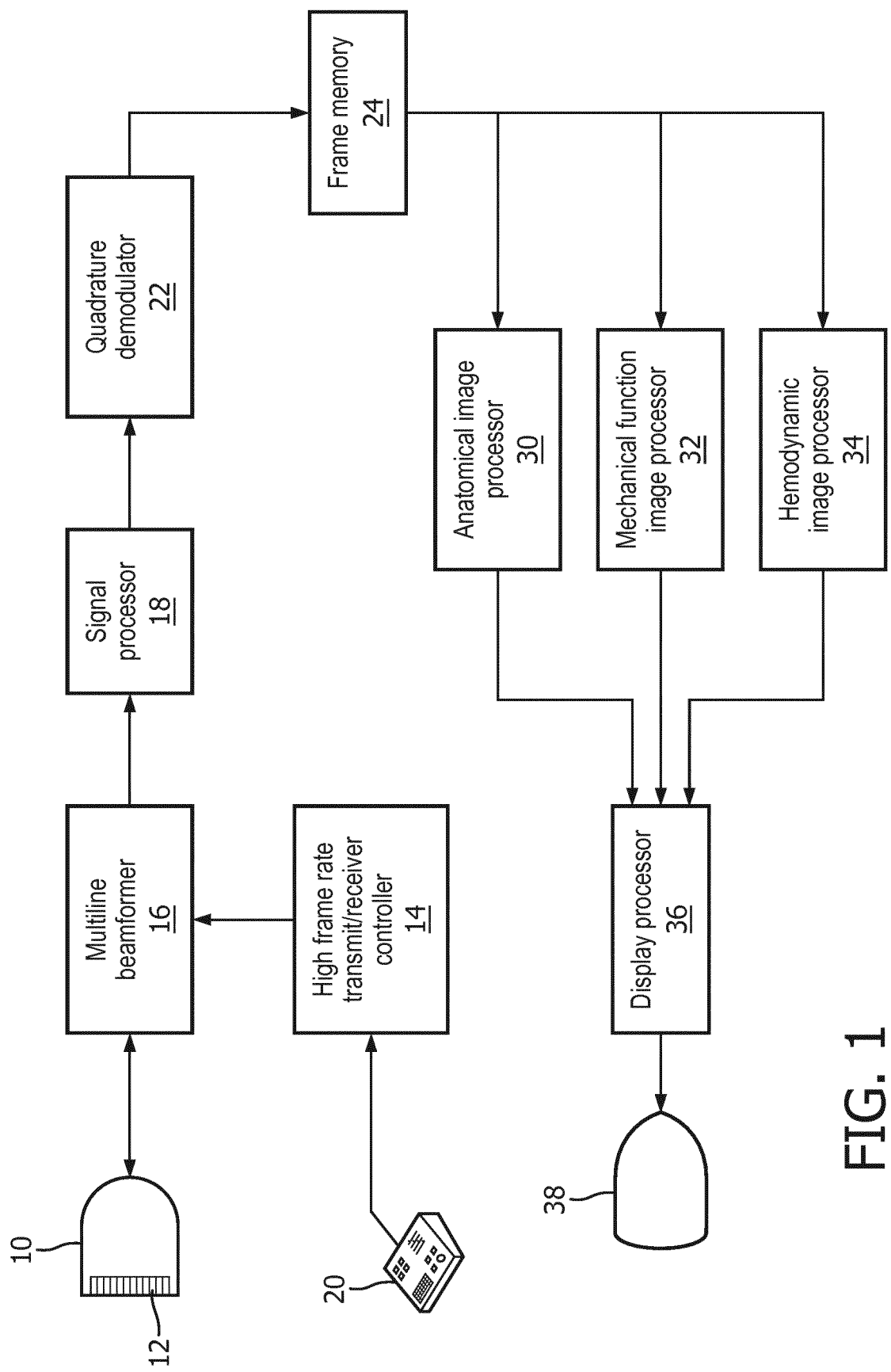
FIG. 1 illustrates in block diagram form an ultrasound system constructed in accordance with the principles of the present invention.

FIG. 1 illustrates in block diagram form a triple mode ultrasonic imaging system constructed in accordance with the principles of the present invention. An ultrasound probe 10 has an array transducer 12 which transmits ultrasound waves to and receives echoes from a region of a body. The array transducer can be a one-dimensional array of transducer elements or a two-dimensional array of transducer elements for scanning a two dimensional image field or a three dimensional image field in the body. The elements of the array transducer are driven by a beamformer, e.g., a multiline beamformer, 16 with timed transmit pulses applied to the elements to cause the array to transmit a broad diverging beam over some or all of the image field. Alternatively, plane waves and mildly focused beams can be used. Typically, shorter pulses will produce better spatial resolution and longer pulses favor Doppler sensitivity. So-called "fat" transmit beams for multiline receive beam acquisition are described in U.S. Pat. No. 4,644,795 (Augustine). Synchronized control of the multiline beamformer is effected by a high frame rate transmit/receive controller 14, which in turn is responsive to user controls of a control panel 20 for selection of characteristics such as beam width, number of beams to be transmitted over the image field, transmit frequency, acquisition frame rate, and so forth. In accordance with one aspect of the present invention, the transmit/receive controller causes the multiline beamformer to transmit beams and acquire frames of echo data at a high frame rate, preferably at least 800 Hz. As discussed for two exemplary acquisition sequences described below, a frame of echo data can be scanned with four beams to acquire an entire frame of echo data at a rate of 1.25 kHz, or a frame can be insonified with a single beam to acquire an entire frame of echo data at a 5 kHz frame rate of acquisition. The controller 14 also controls the processing of multiline beams by the beamformer 16. In one embodiment, the received multiline beams produced simultaneously by the multiline beamformer is 32 beams; however, any number of multiline beams can be used. A suitable multiline beamformer is described in U.S. Pat. No. 8,137,272 (Cooley et al.) The multiline beamformer receives echoes from the transducer elements and combines them to simultaneously form coherent echo signals from points in the image field aligned along thirty-two receive line positions. As will be readily appreciated by one of ordinary skill in the art, many types of beamforming, such as pixel-based beamforming, can be used for the present invention, including software beamforming or hardware beamforming as generally well known in the art. In some embodiments, the beamformer can be an adaptive beamformer. The adaptive beamformer can be used, e.g., to regain spatial resolution from unfocused transmit beams such as the plane waves. In each approach for beamforming, a frame can be generated to correspond to a image field of view that has a depth into the tissue and width depending on the dimensions of the transducer and/or the beam profile. Frames can be 2D or 3D.

The received signals undergo signal processing such as decimation, filtering, harmonic separation and frequency compounding by a signal processor 18. The received echo signals are demodulated into quadrature (I and Q) samples by a quadrature demodulator or quadrature bandpass (QBP) filter 22. The QBP filter can also provide band limiting and bandpass filtering of the received signals. The processed echo signals from one frame acquired from the image field are stored in a frame memory 24 where the echo data may be stored as a corner turning memory for use in a Doppler subsystem of the present invention as discussed below. The frame memory 30 is a RAM, hard drive, removable media memory, digital video disk, compact disk, magnetic media buffer, combinations thereof or other now known or later developed devices for storing ultrasound data.

In accordance with the principles of the present invention the echo signals stored in the frame memory 24 are applied to an anatomical image processor 30, a mechanical function image processor 32, and a hemodynamic image processor 34. These processors access echo signals from the same common group of acquired frames of echo signals stored in the frame memory 24 and process them to produce images in three imaging modes, simultaneously producing a structural anatomic image, an image of mechanical tissue function, and an image of hemodynamic flow. Thus, a single transmit mode is used to acquire echo signals for processing by all three image processors, rather than an interleave of specialized transmit modes used in systems of the prior art. Furthermore, frames may correspond to a image field of view that has a depth into the tissue and width depending on the dimensions of the transducer and/or the beam profile. Frames can be 2D or 3D. Using frames can enable motion estimation calculations on 2D or 3D kernels that can, e.g., decrease noise for motion estimate calculations. Preferably anatomical imaging, mechanical function, and blood flow measurement are done simultaneously using a common transmit pulse sequence. The high frame acquisition rate enables the use of arbitrarily (e.g., infinite) long echo ensemble lengths for velocity imaging and measurement and allow many displacement estimates to be combined into one. For example, ensemble lengths correspond to the number of frames used to produce one motion estimate. Different ensemble lengths may be desired for different imaging modes, e.g., longer ensemble lengths may be needed for Color Doppler imaging as compared to tissue motion imaging. Moreover, the coherence from frame to frame enables the use of frame averaging for enhanced anatomical imaging while surrounding blood flow de-correlates. The three processors, as well as the display processor described below, are each constructed as one of a general processor, a control processor, a digital signal processor, an application specific integrated circuit, a field programmable gate array, a digital circuit, an analog circuit, combinations thereof or other now known or later developed device for processing ultrasonic image data. The resultant three images are coupled to a display processor 36, which arranges the images in a side-by-side or overlaid display format as commanded by the user and forwards them to an image display 38 at a display frame rate of 30 Hz or faster. A display frame rate of 100-150 Hz should be sufficient to depict all physiologically relevant heart motion, for instance. Since the images are formed simultaneously from the same acquisition frames which themselves are acquired at a high acquisition frame rate, there is excellent correspondence of the structure, function and dynamics represented in all three images. A single image can be frozen on the display 38, showing all three characteristics as they appear in the body at the same instant in time.

Figure 2A:
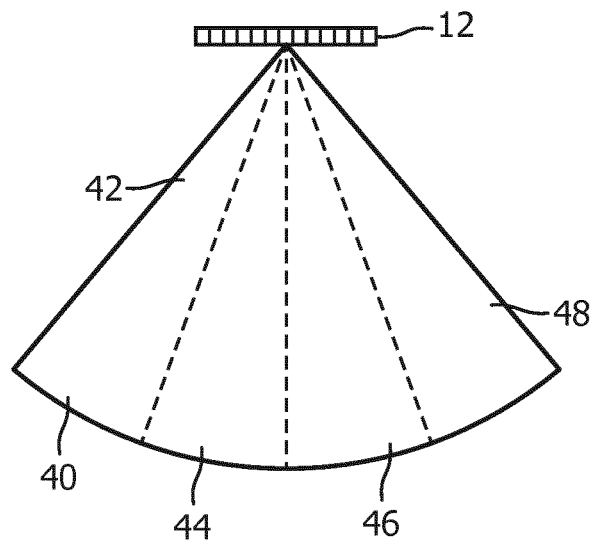
FIGS. 2a and 2b illustrate two sector image fields scanned by four and one transmit beams, respectively.
Figure 2B:
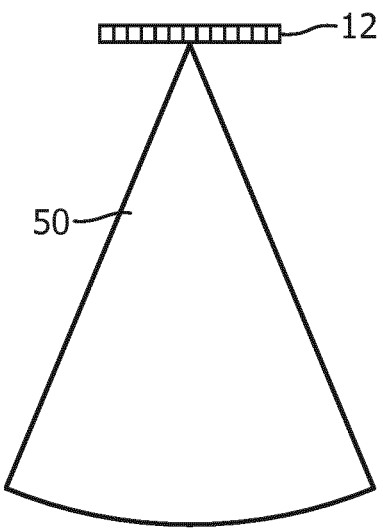
Figure 2C:
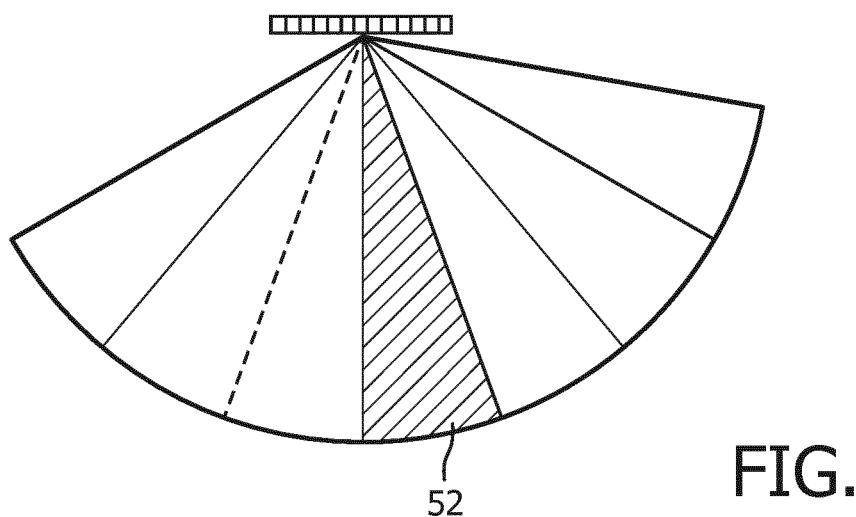
FIG. 2c illustrates an embodiment of using coherent compounding for the present invention.

FIGS. 2a and 2b show two examples of scanning a sector-shaped image field in accordance with the present invention. In FIG. 2a a wide sector image 40, e.g., a 90° sector, is scanned with four divergent transmit beams, each insonifying one-quarter of the sector, shown as sub-sector 42, sub-sector 44, sub-sector 46, and sub-sector 48. When the transmit beam frequency is 5 kHz, (one transmit beam every 200 microseconds), the acquisition frame rate for a four-beam image is 1.25 kHz (one frame every 800 microseconds.) FIG. 2b illustrates a second example, in which the entire sector image 50 is scanned by a single beam. In this example, when the transmit beam frequency is 5 kHz, the acquisition frame rate is 1.25 kHz. Alternatively, the sector 50 can be scanned in an odd-line, even-line format. Following transmission of a first beam insonifying the image field, the multiline beamformer 16 can form lines 1, 3, 5, etc. of the image. Following transmission of a second beam, the multiline beamformer forms interspersed lines 2, 4, 6, etc., thereby improving spatial resolution. The acquisition frame rate will be halved, of course, due to the use to two transmit beams. Preferably the acquisition frame rate is in the range of ~1 to 4 kHz, and in some embodiments at a 2.5 kHz acquisition frame rate. At such a high frame rate, a large number of acquisition frames can be coherently combined to improve signal-to-noise ratio, and long ensembles of echo data can be used to produce precise Doppler or motion estimates at any point in or over an entire image frame. FIG. 2c shows the example of scanning a sector-shaped image field using coherent compounding. Similar to FIG. 2a, the four transmit beams are used in FIG. 2c in which coherent compounding of the transmit beams is performed in the overlap region 52.

Figure 3:
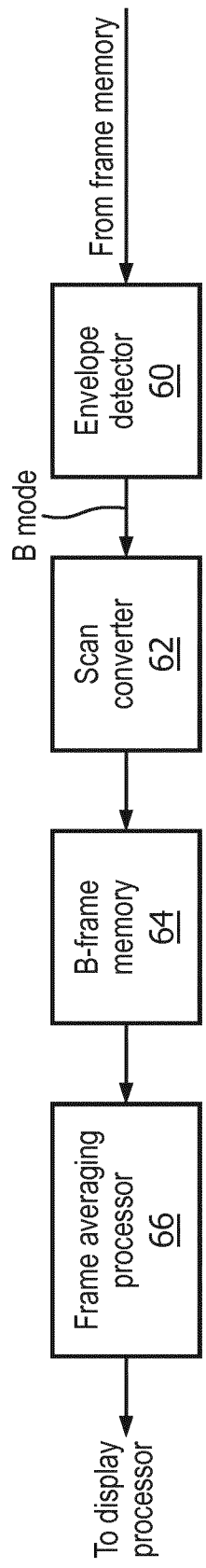
FIG. 3 illustrates in block diagram form an implementation of the anatomical image processor of FIG. 1 in the form of a B mode processing and display subsystem.

FIG. 3 shows an example of anatomical image processor 30 of FIG. 1, a B mode processing chain of components. The quadrature (I,Q) data from the frame memory 24 is applied to an amplitude or envelope detector 60. The envelope detector processes I,Q echo data by executing the equation $(I^2+Q^2)^{1/2}$ for formation of data values of a B mode image of tissue structure. These detected data points are converted from their acquired format, r-θ in the sector image fields of FIGS. 2a and 2b, to Cartesian (x-y) coordinates, suitable for display on a raster scanned display, by a scan converter 62. The scan converter may also fill in surrounding display data points by interpolating between acquired data values, e.g., four-point interpolation. The scan converted image data is stored in a B frame memory 64. To improve the signal-to-noise ratio of the image data from the divergent transmit beams, the frames of image data stored in the B frame memory may be temporally averaged over a number of frames, such as 40 frames, by a frame averaging processor 66. Alternatively, averaging can occur prior to envelope detection on quadrature date. Here, the frame averaging processor performs a point-by-point averaging of each corresponding point in up to 40 successive acquired images of the B frame memory. The resulting enhanced B mode image is coupled to the display processor 36.

Figure 4A:
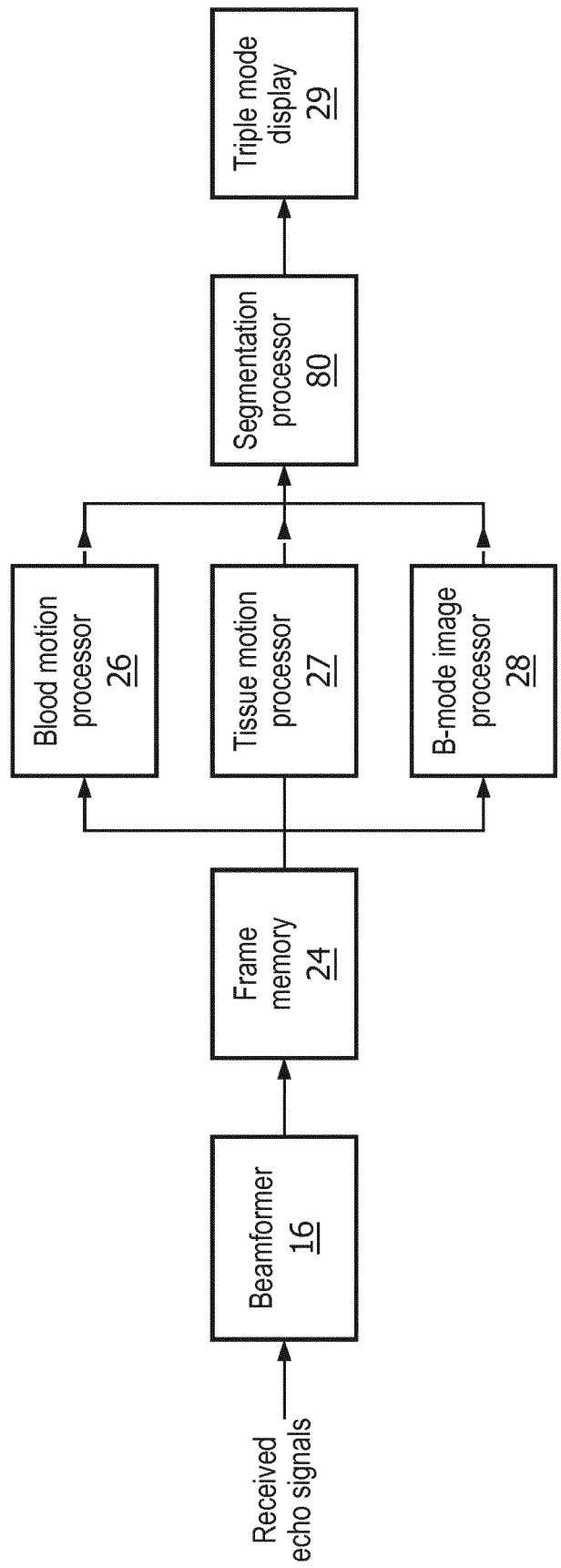
FIG. 4A illustrates in block diagram form an implementation of a blood motion processor, a tissue motion processor, and a B-mode image processor according to an embodiment of the present invention.
Figure 4B:
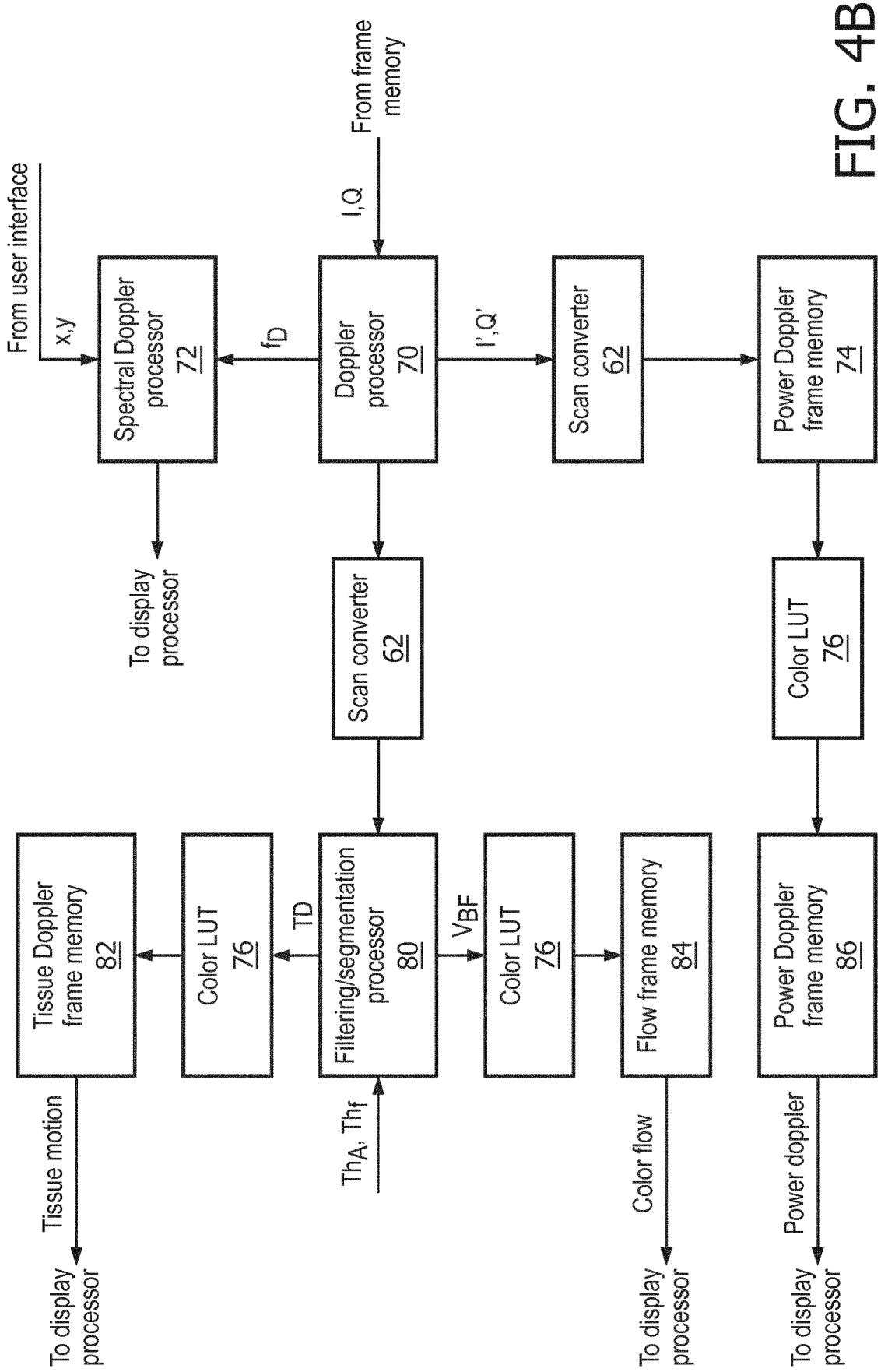
FIG. 4B illustrates in block diagram form a Doppler implementation of the anatomical image, mechanical function, and hemodynamic image processors of FIG. 1.

FIG. 4A illustrates an example triplex imaging ultrasound system in accordance with the present invention. As described herein, a common transmit pulse sequence can be used to generate receive echo signals that can be processed for use in generating data for three different imaging modes. As shown, received echo signals generated from the common transmit pulse sequence are received by a beamformer 16. The beamformer, in some examples, can be a multiline beamformer as described, e.g., in U.S. Pat. No. 8,137,272, which is incorporated by reference herein. The beamformed RF data can be stored in a frame memory 24, which can provide the beamformed data for processing by three different processors: a blood motion processor 26, a tissue motion processor 27, and a B-mode image processor 28. It will be generally understood that with respect to this embodiment and other examples provided herein that the present invention encompasses different processors, but also the processing can be accomplished on one processor configured to perform all the three functions. The blood motion processor, the tissue motion processor, and the B-mode image processor generate blood motion data, tissue motion data, and B-mode image data, respectively. The blood motion data, tissue motion data, and B-mode image data are received by the segmentation processor 80, which is configured to segment out tissue Doppler signals TD and apply them to a color look-up table (LUT) 76 and to segment out higher frequency blood flow velocities $v_{BF}$ and applying them to another color look-up table 76 as described further herein. After segmentation, the image data from the three different imaging modes can be displayed on the triple mode display 29. FIG. 4B illustrates a triplex imaging system which, in this example, produces both a mechanical function image, a tissue motion image, and three hemodynamic image processing chains which produce a color flow image, a power Doppler image, and a spectral Doppler image. The illustrated Doppler subsystem also produces flow information at a particular point in an image, a spectral Doppler display. A Doppler processor 70 receives ensembles of temporally acquired I,Q echo data from a sequence of sequentially acquired frames stored in the frame memory 24.

The organization of frame memory 24 as a corner-turning memory facilitates this operation. The Doppler processor 70 may employ different processing techniques such as fast Fourier transform (FFT) processing or correlation processing, as is well known in the art. In the illustrated embodiment of the present invention autocorrelation processing is used. An ensemble of samples from each point on a Doppler image line, typically ranging from 10 to 40 samples per ensemble (from 10 to 40 frames of frame memory 24) is input into the Doppler processor 70. An ensemble of fewer samples may be used for display of moving tissue due to the higher signal-to-noise ratio of tissue echoes as compared to echoes from blood flow. The sample data is processed in quadrature I,Q form. An autocorrelator multiplies adjacent samples in the sequence of samples in complex conjugate form and sums the products to produce a result in the form of I'+jQ'. Mathematically the autocorrelation process can be expressed as $$X' = \sum_{k=1}^{n-1} X_{k+1} \cdot X_k^*$$

where $X_k = I_k + jQ_k$ and n is the number of samples in the sequence. From the complex result the Doppler phase shift $\phi_D$ is calculated as the arc tangent of the quotient of Q' and I', or $$\phi_D = \tan^{-1} \frac{Q'}{I'}$$

The Doppler frequency shift $f_D$ is determined by multiplying the phase shift $\phi_D$ by the PRF (frame acquisition rate frequency) and dividing by $2\pi$:

$$f_D = \phi_D \frac{PRF}{2\pi}$$

The velocity of the motion is then estimated from the Doppler velocity equation by the equation $$v = \frac{f_D c}{2 f_o \cos\theta}$$

by assuming $f_o$ to be the center frequency of the transmitted waveform.

In one implementation of the present invention two dimensional motion estimation is used, for example implemented as a 2-dimensional autocorrelation as described in U.S. Pat. No. 5,386,830 (Powers et al.) The velocities thus determined may be used in a color flow display by overlaying or blending Doppler color-coded pixels with the B mode image or in a spectral Doppler display of spectral lines. Other Doppler and motion data such as flow direction, variance, acceleration and power may also be determined from this Doppler data and displayed on the display 38.

Figure 5:
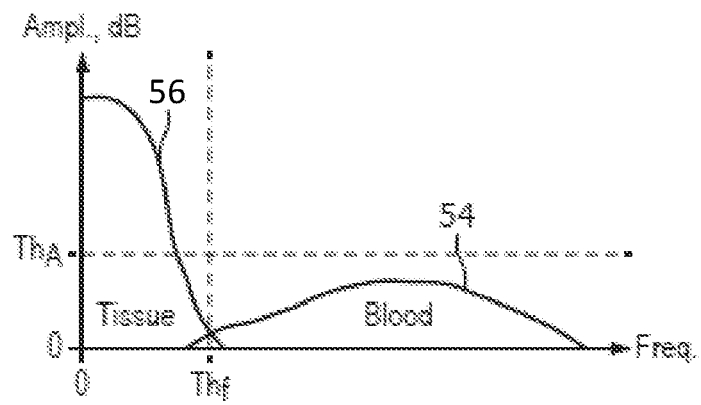
FIG. 5 is a graph illustrating the tissue and blood flow segmentation used by the system of FIG. 4.

The velocity estimates, which are proportional to the Doppler frequency shift, are converted to Cartesian space by a scan converter 62, then applied to a filtering and segmentation processor 80. Segmentation can be performed by filtering, which can include a process in which stronger tissue signals in the low frequency band 56 of FIG. 5 would be canceled by a high pass filtering characteristic which filters out signals below a frequency $Th_f$. Tissue signals are generally lower in frequency than blood flow because the velocity of tissue motion is generally less than that of flowing blood, and the blood flow frequencies (velocities) in band 54 would be processed for display. A typical threshold used to segment (separate) moving tissue velocities from blood flow velocities is 10 cm/sec. The tissue and blood bands of FIG. 5 also illustrate that the tissue motion signals can be segmented by filtering out frequencies above threshold frequency $Th_f$, eliminating signals below an amplitude threshold $Th_A$, or both. The filtering and segmentation processor 80 does both, segmenting out tissue Doppler signals TD and applying them to a color look-up table (LUT) 76 and segmenting out higher frequency blood flow velocities $v_{BF}$ and applying them to another color look-up table 76. These two LUTs (as well as other LUTs in the system) can be the same by multiplexing their use between tissue signals and blood flow signals. The color values corresponding to tissue Doppler values TD are stored in a tissue Doppler frame memory 82, and the color values corresponding to blood flow velocity values $v_{BF}$ are stored in a flow frame memory 84. Tissue Doppler frame memory 82 thus retains an overlay of color values depicting tissue motion, which are coupled to the display processor 36 when the user wants to assess tissue motion overlaying tissue in a structural (B mode) image. Flow frame memory 84 similarly retains an overlay of color values depicting blood flow velocity, which are coupled to the display processor 36 when the user wants to assess flow velocities overlaying vessel lumens in a structural (B mode) image.

The Doppler processor 70 provides I',Q' values to a scan converter 62 for spatial coordinate conversion, which are then applied to a power Doppler estimator 74. The estimator 74 estimates power Doppler values by the equation $(I'^2 + Q'^2)^{1/2}$ which are then converted to corresponding color values by a color LUT 76. These color values, representing the intensity of the Doppler signal at locations in the image field, are stored in a power Doppler frame memory 86. A frame stored in memory 86 is coupled to the display processor 36 for overlay over the tissue or blood flow (or both) of a structural (B mode) image when the user wants to assess the intensity of the Doppler signals from motion in points in an image. Power Doppler signals can be segmented in amplitude using a threshold similar to $Th_A$ when the user want to display power Doppler intensities of only moving tissue or only blood flow.

The Doppler frequency shift values generated for a particular point x,y in an image are used by a spectral Doppler processor 72 to produce a spectrogram of flow velocities at that point. The user manipulates a user control to apply the x,y values for a selected point in an image to the spectral Doppler processor. The spectral Doppler processor operates as is well known in the art to produce a time sequence of flow velocity distribution for flow at the point in the image, which is coupled to the display processor for display as a spectrogram. See, e.g., U.S. Pat. No. 5,287,753 (Routh et al.), U.S. Pat. No. 6,464,637 (Criton et al.) and U.S. Pat. No. 7,815,572 (Loupas) for details on construction and operation of a spectral Doppler processor.

Figure 6:
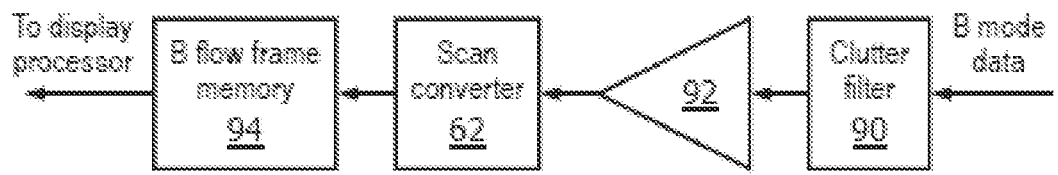
FIG. 6 illustrates in block diagram form an implementation of another hemodynamic image processor in the form of a B-flow subsystem.
Figure 6A:
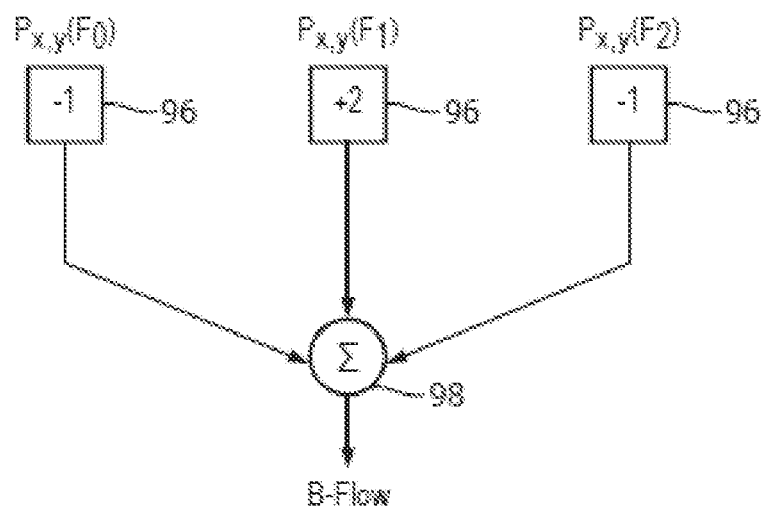
FIG. 6a illustrates one implementation of the clutter filter of FIG. 6.

Another hemodynamic display processor is illustrated in FIG. 6, which is a B-flow image processing chain. B-flow displays the intensity of clutter-filtered B mode data. A clutter filter 90 removes stationary and slowly moving targets from the B mode echo data. The clutter filter can be as simple as a 2-tap filter, but with the high acquisition frame rate much longer filters can also be used. FFT-based (fast Fourier transform) filtering has been found to be effective for the clutter filter 90. FIG. 6a illustrates a 3-tap clutter filter implementation in which the signals from the same point ($P_{x,y}$) in three successive frames ($F_0$, $F_1$, and $F_2$) are applied to weighting circuits 96 to weight the applied signals by [−1], [+2], and [−1], respectively. The weighted signals over the three-frame interval are combined by a summer 98 to produce clutter-reduced data. The number of taps used depends on the expected range of motion of the tissue or blood flow, with faster motion requiring shorter filters, and the bandwidth around DC that one wishes to reject. Thresholding can also be used to segment tissue motion and blood flow as discussed above. Since the B-flow signals are from blood cells and low in amplitude, a variable gain amplifier 92 is used to amplify the signals, which are then converted to the desired display format by scan converter 62. Frames of B-flow signal data are stored in B-flow frame memory 94, from which they are applied to the display processor 36. The B-flow can be displayed as an overlay in the vessels of a structural (B mode) image in the same manner as color flow Doppler is displayed.

Figure 7:
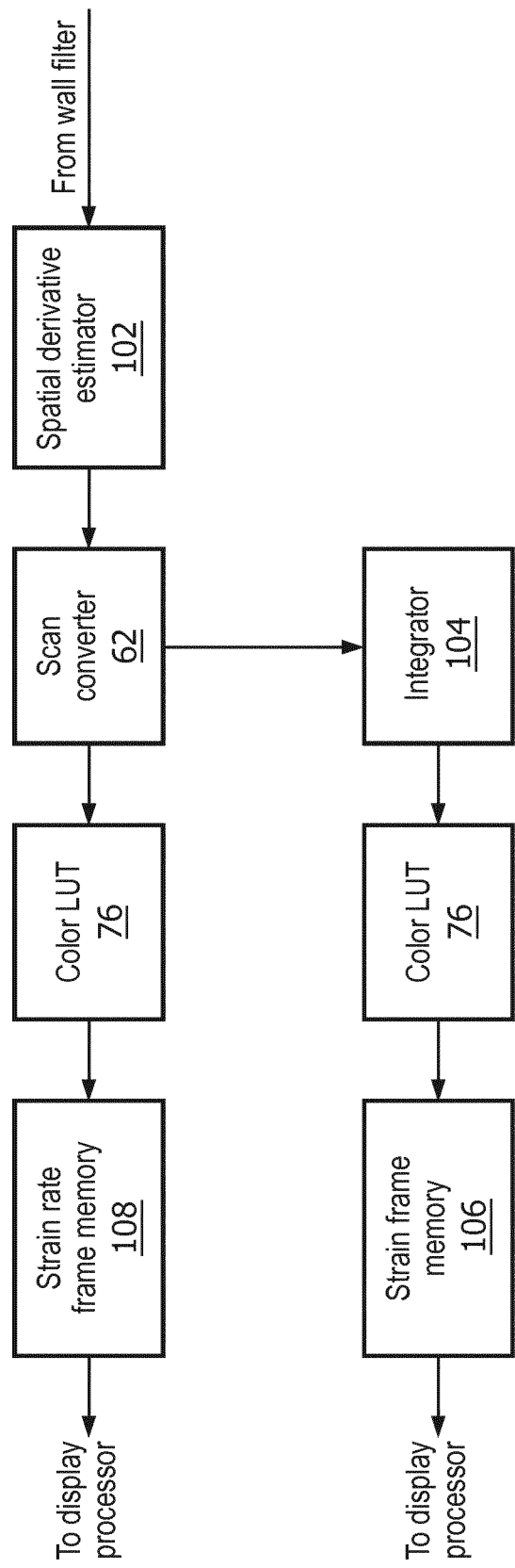
FIG. 7 illustrates in block diagram form another implementation of a mechanical function image processor in the form of a strain and strain rate imaging subsystem.

FIG. 7 illustrates a processing chain that produces two more mechanical function images, in this case, strain and strain rate. Strain rate is the spatial derivative of the velocity of moving tissue, and strain is the temporal integral of strain rate. See, e.g., U.S. Pat. No. 6,537,221 (Criton et al.) A spatial derivative estimator 102 computes strain rate values by taking the derivative (difference) of consecutive velocity values along a beam, which values are produced by the Doppler processor 70. Alternatively, the derivative can be taken of velocity values in the direction of motion as described in the foregoing Criton et al. patent. These values are produced as the tissue Doppler (TD) values by the filtering and segmentation processor 80. The strain rate values are scan converted by a scan converter 62 if scan conversion has not been performed previously. The strain rate values from points in a tissue image are integrated over time by an integrator 104 to produce strain values. The frames of strain rate values and strain values are applied to color LUTs 76 for conversion into corresponding color values and these values are stored in strain rate frame memory 108 and strain frame memory 106, respectively, from which they may be coupled to the display processor 36 when the user wants to assess the mechanical characteristics of strain or strain rate of tissue.

Figure 8:
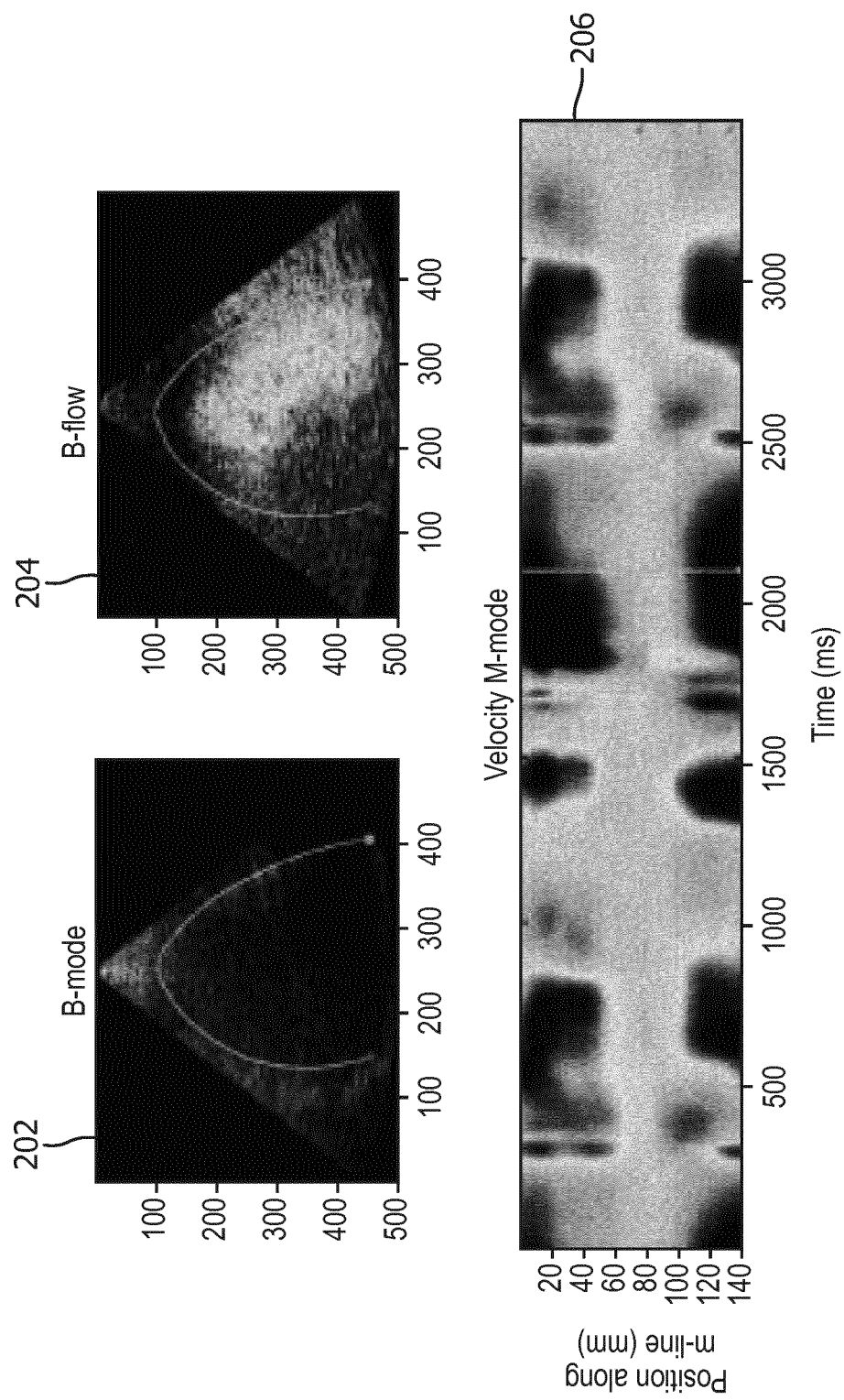
FIG. 8 illustrates a triple mode image display produced by an implementation of the present invention.
Figure 9:
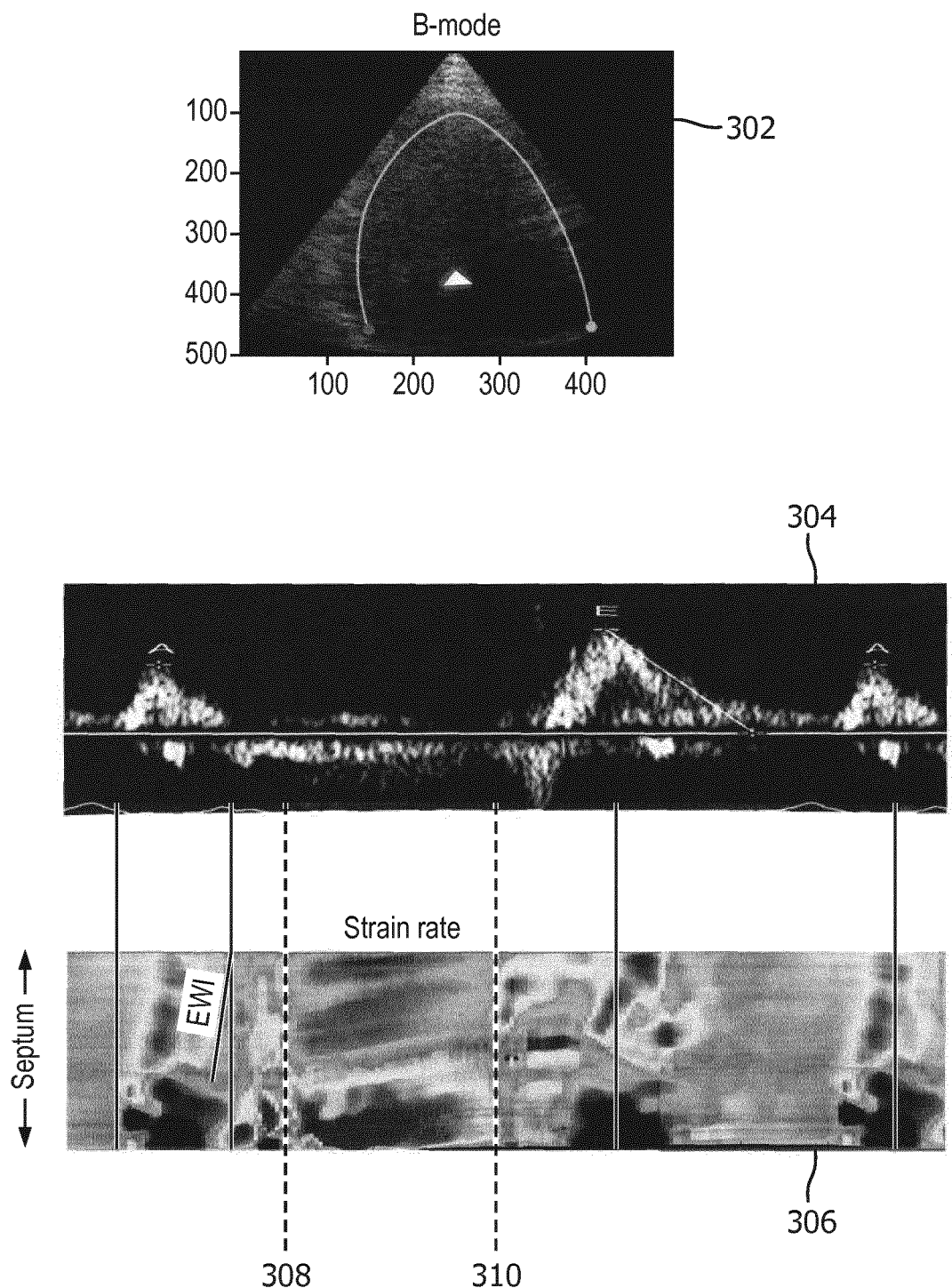
FIG. 9 illustrates another triple mode image display produced by an implementation of the present invention.

FIGS. 8 and 9 provide two examples of how anatomical, mechanical function, and hemodynamic images can be displayed simultaneously for assessment of all three characteristics and their interaction in the body of a subject. At the upper left of the display screen of FIG. 8 is an anatomical B mode image 202 of the left ventricle of a heart. This image and the others on the screen in this example were produced from image data acquired by repeatedly scanning a sector-shaped image field with two beams, one insonifying the left side of the sector and the other insonifying the right side of the sector. On receive, thirty-two multilines were received and processed in parallel from each side of the sector, thereby producing image frames of sixty-four scanlines which were stored in the frame memory 24. The acquisition frame rate was 2.5 kHz. Multiple B mode frames, up to twenty frames in this example, were averaged point-by-point by the frame averaging processor 66 to produce B mode images with good signal to noise ratio on the display. A trace of the border of the left ventricular heart chamber was drawn over the image as shown in the drawing, which may be drawn manually or by automated border tracing as described in the aforementioned U.S. Pat. No. 6,537,221 (Criton et al.) To the right of the anatomical image is a hemodynamic image, B-flow image 204, of the left ventricle. The same chamber border is traced over the B-flow image. The brighter pixels on the right side of the B-flow image show faster flowing blood in the right side of the heart chamber. At the bottom of the screen is a mechanical function image, a velocity M-mode image 206 of tissue Doppler values showing the velocity of the tissue at each point around the border tracing. An M-mode image displays the mechanical dynamics along a line over an image as they change with time along the horizontal time axis. Each vertical line of the M-mode image represents a particular instant in time, and the colors from top to bottom along each vertical M-line of the images illustrate the instantaneous velocity of the tissue at each point along the border tracing. Observing the M-mode image from left to right shows the variation in velocity of the tissue at the left ventricular border with time. The three images of FIG. 8 are all temporally synchronous as they were produced from the same image data in the frame memory, and they enable a clinician to evaluate the structural, mechanical function and hemodynamic characteristics of the left ventricle on the same display screen. When played as a loop or continuously in real time, the structure of the left ventricle will expand and contract in size with each heartbeat, blood flow will be seen to increase and decrease in speed in the chamber with each contraction and relaxation, and the mechanical speed of the ventricular border tissue will increase and decrease at different rates at different locations around the chamber over the heart cycle.

The second example of a triple mode display in FIG. 9 displays an anatomical B mode image 302 of the left ventricle at the top of the screen, again with the left ventricular border traced over the image. Toward the bottom of the heart chamber and above the mitral valve the clinician has positioned a triangular cursor which is the location at which a spectral Doppler flow measurement is to be taken. The spectral Doppler image 304 is shown in the center of the screen. At the bottom of the screen is a color M-mode image 306 of strain rate, acquired along the tissue of the septal wall at the center of the heart. The dotted lines 308 and 310 demarcate two functional landmarks of the heart cycle, the closing of the mitral valve at 308 and the peak ventricular strain in the septum at 310. With this triple mode display the clinician can assess the structure of the heart as well as the mechanical and fluid dynamics of the strain rate in the septum and the variation in blood flow velocity at a selected point in the heart chamber.

It should be noted that the various embodiments described above and illustrated by the exemplary ultrasound system of FIGS. 1-7 may be implemented in hardware, software or a combination thereof. The various embodiments and/or components of an ultrasound system, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system. The computer or processor may also include a memory. The memory devices described above for the frame memories may include Random Access Memory (RAM) or other data storage devices, including a storage device, which may be a hard disk drive or a removable storage drive such as a floppy disk drive, optical disk drive, solid-state thumb drive, and the like. The storage device may also be other similar means for loading computer programs or other instructions into the computer or processor.

The set of instructions of an ultrasound system such as that described above generally include various commands that instruct the computer or processor as a processing machine to perform specific operations such as the methods and processes of the various embodiments of the invention. The set of instructions is typically in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands entered via the control panel 20, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

The invention claimed is:

1. An ultrasonic imaging system for producing a triple mode display of multiple different modes of images at a high acquisition frame rate comprising:
   an ultrasound probe having an array transducer;
   a multiline beamformer, wherein the beamformer is coupled to the array transducer, wherein the multiline beamformer is arranged to acquire frames of echo signals from a single transmit mode at the high acquisition frame rate;
   a frame memory, wherein the frame memory is arranged to store the frames of echo signals, wherein the echo signals are acquired at the high acquisition frame rate, wherein the frames comprise echo signals corresponding to an image field of view;
   an anatomical image processor circuit, wherein the anatomical image processor circuit is coupled to the frame memory, wherein the anatomical image processor circuit is arranged to produce anatomical images from the frames of echo signals corresponding to the image field of view from the single transmit mode;
   a mechanical function image processor circuit, wherein the mechanical function image processor circuit is coupled to the frame memory, wherein the mechanical function image processor circuit is arranged to produce mechanical function images from the frames of echo signals corresponding to the image field of view from the single transmit mode at a mechanical function echo ensemble length;
   a hemodynamic image processor circuit, wherein the hemodynamic image processor circuit is coupled to the frame memory, wherein the hemodynamic image processor circuit is arranged to produce blood flow images from the frames of echo signals corresponding to the image field of view from the single transmit mode at a hemodynamic echo ensemble length; and
   a display coupled to the anatomical image processor circuit, the mechanical function image processor circuit, and the hemodynamic image processor circuit, wherein the display is arranged to display images from the anatomical image processor circuit, the mechanical function image processor circuit, and the hemodynamic image processor circuit simultaneously and side-by-side, wherein the hemodynamic echo ensemble length is longer than the mechanical function echo ensemble length.

2. The ultrasonic imaging system of claim 1, wherein the multiline beamformer is arranged to acquire frames of echo signals at the high acquisition frame rate of at least 800 Hz.

3. The ultrasonic imaging system of claim 1, wherein the multiline beamformer is arranged further configured to scan the image field with at least one diverging transmit beam, plane wave, or unfocused beam.

4. The ultrasonic imaging system of claim 3, wherein the multiline beamformer is arranged to produce at least 32 received multilines in response to a diverging transmit beam.

5. The ultrasonic imaging system of claim 1, wherein the anatomical image processor circuit, the mechanical function image processor circuit, and the hemodynamic image processor circuit are arranged to produce images using a common group of the echo signals.

6. The ultrasonic imaging system of claim 5, wherein the multiline beamformer is arranged to use a common transmit pulse sequence,
   wherein the multiline beamformer receives the echo signals,
   wherein the echo signals are used by the anatomical image processor circuit, the mechanical function image processor circuit, and the hemodynamic image processor circuit.

7. The ultrasonic imaging system of claim 1, wherein the anatomical image processor circuit further comprises a B mode processor circuit arranged to produce B mode images of anatomical structure.

8. The ultrasonic imaging system of claim 1, further comprising a quadrature demodulator having an input coupled to the multiline beamformer and an output coupled to the frame memory.

9. The ultrasonic imaging system of claim 8, wherein the mechanical function image processor circuit comprises a motion processor circuit arranged to produce tissue Doppler images, a strain rate image processing chain, or a strain image processing chain.

10. The ultrasonic imaging system of claim 8, wherein the strain rate image processing chain and the strain image processing chain comprise a spatial derivative estimator.

11. The ultrasonic imaging system of claim 10, wherein the spatial derivative estimator is coupled to receive signals of tissue velocity.

12. The ultrasonic imaging system of claim 8, wherein the hemodynamic image processor circuit comprises one or more of a color flow processing chain, a power Doppler processing chain, a spectral Doppler processor circuit, a B-flow processing chain, or a vector flow processing chain.

13. The ultrasonic imaging system of claim 12, wherein the hemodynamic image processor circuit is arranged to segment tissue motion and flow by filtering according to a frequency threshold.

14. The ultrasonic imaging system of claim 12, wherein the B-flow processing chain further comprises a clutter filter arranged to pass B mode signals of blood flow.

* * * * *